United States Patent [19]

Krabetz et al.

[11] 4,259,211
[45] Mar. 31, 1981

[54] CATALYST FOR THE OXIDATION OF ACROLEIN AND METHACROLEIN TO ACRYLIC ACID AND METHACRYLIC ACID, RESPECTIVELY

[75] Inventors: Richard Krabetz, Kirchheim; Walter Herrmann, Mannheim; Norbert Scholz, Ludwigshafen; Heinz Engelbach, Limburgerhof; Gerd-Juergen Engert, Frankenthal; Carl-Heinz Willersinn, Ludwigshafen; Gerd Duembgen, Dannstadt-Schauernheim; Fritz Thiessen, Ludwigshafen, all of Fed. Rep. of Germany

[73] Assignee: BASF Aktiengesellschaft, Fed. Rep. of Germany

[21] Appl. No.: 963,203

[22] Filed: Nov. 24, 1978

Related U.S. Application Data

[63] Continuation of Ser. No. 800,722, May 26, 1977, abandoned.

[30] Foreign Application Priority Data

Jun. 16, 1976 [DE] Fed. Rep. of Germany ....... 2626887

[51] Int. Cl.³ .................... B01J 23/22; B01J 23/28; B01J 23/30; B01J 23/72
[52] U.S. Cl. .................... 252/443; 252/455 R; 252/456; 252/462; 252/464; 252/467; 252/469; 252/470; 562/534; 562/535
[58] Field of Search ............... 252/467, 470, 456, 464, 252/443, 455 R, 462, 469; 562/534, 535

[56] References Cited

U.S. PATENT DOCUMENTS

| 3,567,773 | 3/1971 | Yamaguchi et al. | 252/467 X |
| 3,736,354 | 5/1973 | Yanagita et al. | 252/456 X |
| 3,773,692 | 11/1973 | Hensel et al. | 252/455 R |
| 3,773,828 | 11/1973 | Kadowaki et al. | 252/467 X |
| 3,956,377 | 5/1976 | Dolhyj et al. | 252/462 X |
| 3,988,359 | 10/1976 | Saito et al. | 260/465.3 |
| 4,035,262 | 7/1977 | Childress et al. | 252/467 X |
| 4,111,983 | 9/1978 | Kurtz et al. | 252/467 X |
| 4,138,366 | 2/1979 | Shaw et al. | 252/467 X |
| 4,157,987 | 6/1979 | Dolhyj et al. | 562/534 |

FOREIGN PATENT DOCUMENTS

| 2448804 | 4/1975 | Fed. Rep. of Germany . | |
| 4961186 | 6/1974 | Japan | 562/534 |
| 1387776 | 3/1975 | United Kingdom . | |

Primary Examiner—W. J. Shine
Attorney, Agent, or Firm—Keil & Witherspoon

[57] ABSTRACT

Catalysts which consist of a molded carrier, the surface of which is coated with an active catalyst composition of the general formula $Mo_{12}A_aB_bC_cD_dO_x$, where A is V and/or W, B is Cu and/or Fe and/or Mn and/or Ni and/or Cr, C is Nb and/or Ta and/or Bi and/or Sb and/or Sn and/or Th and/or Ce and/or U, D is Li and/or Na and/or K and/or Rb and/or Cs and/or Tl and a is from 0.1 to 18, b is from 0 to 8, c is from 0 to 10, d is from 0 to 2 and x is from 36 to 135, which are particularly active and selective for the oxidation of acrolein and methacrolein with oxygen-containing gases to give acrylic acid and methacrylic acid, respectively, are obtained by first manufacturing the catalyst composition, before applying it to the carrier, from thermally easily decomposed salts of the components by mixing aqueous solutions, slurries or moist solid masses of the salts of the components, drying the mixture and calcining the dried composition at from 140° to 600° C., then milling it to a particle size of less than 150 μm and thereafter applying it, as a mixture with water, as a layer from 10 to 1,500 μm thick, to the premolded carrier, which has a rough surface.

8 Claims, No Drawings

CATALYST FOR THE OXIDATION OF ACROLEIN AND METHACROLEIN TO ACRYLIC ACID AND METHACRYLIC ACID, RESPECTIVELY

This is a continuation of application Ser. No. 800,722, filed May 26, 1977, now abandoned.

The present invention relates to a new catalyst for the gas phase oxidation of acrolein and methacrolein to give acrylic acid and methacrylic acid, respectively, in which an active catalyst layer is applied to an inert carrier core.

A large number of catalysts containing molybdenum oxide have been disclosed for the gas phase oxidation of acrolein and methacrolein to acrylic acid and methacrylic acid, respectively. As additional activating components, these catalysts in most cases contain vanadium and/or tungsten and may or may not contain iron and/or copper and/or manganese and/or nickel and/or phosphorus as well as niobium and/or tantalum and/or bismuth and/or antimony and/or tin and/or thorium and/or cerium, alkali metals, especially sodium, potassium and cesium, and thallium. Such catalysts are disclosed, for example, in U.S. Pat. No. 3,567,772, Canadian Pat. No. 941,384, British Pat. No. 1,353,864, U.S. Pat. No. 3,773,692, British Pat. No. 1,337,865, British Pat. No. 1,387,776 and German Laid-Open Application DOS No. 2,517,148. They may be represented by the general formula $Mo_{12}A_aB_bC_cD_dP_eO_x$ where A is V and/or W, B is Cu and/or Fe and/or Mn and/or Ni and/or Cr, C is Nb and/or Ta and/or Bi and/or Sb and/or Sn and/or U and/or Th and/or Ce, D is Li and/or Na and/or K and/or Rb and/or Cs and/or Tl, and a is from 0.1 to 18, b is from 0 to 8, c is from 0 to 10, d is from 0 to 2, e is from 0 to 5 and x is from 36 to 136. Oxidic catalysts of this nature may be employed for the gas phase oxidation of acrolein and methacrolein, either unsupported or supported, and in the latter case the inert carriers used are mostly aluminum oxides, silicon dioxide and their mixtures, silicon carbide, titanium dioxide and also zirconium dioxide. To manufacture catalysts of this nature, the common procedure is to mix mixtures of aqueous solutions of salts of the components, eg. of ammonium molybdate, ammonium vanadate, ammonium tungstate and nitrates of iron, copper or manganese, and impregnate the carrier with the mixture, from which the water may or may not have been evaporated completely or partially, or to coat the carrier with the composition. If the composition contains water, the material is dried and calcined, after the water has been evaporated off, the calcination being carried out in most cases at above 150° C., especially at from 180° to 600° C. This gives oxide catalysts which carry the active catalyst composition on the inner and/or outer surface of the carrier. A disadvantage of the supported oxide catalysts thus obtained is that they are sensitive to mechanical stresses resulting from friction, as occurs, eg. in the calcination stages of the process of manufacture or when filling reactor tubes. In addition, their activity and selectivity is in many cases not fully satisfactory. Finally, the active composition is frequently not distributed uniformly over the surface of the carrier. The manufacture of supported catalysts by applying a mixture of the active metal oxides to carriers was proposed in British Pat. No. 1,296,922.

U.S. Pat. No. 3,956,377 discloses a special process for the manufacture of oxide catalysts, in the form of layers, for the gas phase oxidation of acrolein and methacrolein to acrylic acid and methacrylic acid respectively, in which, for example, molybdenum oxide, vanadium oxide and tungsten metal powder are suspended in water by heating under reflux, the resulting slurry is evaporated and the residue is dried for several days at 115° C. The active catalyst composition thus obtained is then applied to the carrier, which has been pre-moistened with water, the application being effected by tumbling the moist carrier with a powder of the active catalyst. Catalysts manufactured in this way are frequently non-selective.

We have found that catalysts for the oxidation of acrolein and methacrolein with oxygen-containing gases to give acrylic acid and methacrylic acid, respectively, which catalysts consist of a conventional molded carrier, the surface of which is coated with an active catalyst composition of the general formula $Mo_{12}A_aB_bC_cD_dO_x$, where A is V and/or W, B is Cu and/or Fe and/or Mn and/or Ni and/or Cr, C is Nb and/or Ta and/or Bi and/or Sb and/or Sn and/or Th and/or Ce and/or U, D is Li and/or Na and/or K and/or Rb and/or Cs and/or Tl and a is from 0.1 to 18, b is from 0 to 8, c is from 0 to 10, d is from 0 to 2 and x is from 36.25 to 135 are particularly advantageous if the catalyst composition, before applying to the carrier, is manufactured from thermally easily decomposed salts of the components by mixing aqueous solutions, slurries or moist solid masses of the salts of the components, drying the mixture and calcining the dried composition at from 140° to 600° C., and is comminuted, for example by milling to a particle size of less than 150 μm, and applied, as a mixture with water, as a layer from 10 to 1,500 μm thick, to the premolded carrier, which has a rough surface.

Suitable carriers for the manufacture of the new oxide catalysts are the conventional inert carriers, for example highly calcined aluminum oxides (preferably in the α-phase), natural and synthetic silicates and aluminosilicates, eg. mullite and steatite, silicon carbide and zirconium oxides and/or titanium oxides. The inner surface area of the carriers may be varied within wide limits and is in general from less than 1 to 20 m²/g, eg. frequently from 1 to 20 m²/g, especially from 1 to 10 m²/g. The porosity is generally not critical and is mostly from 1 to 65%, and from 50 to 85% of the pores have a diameter of from 20 to 1,500 μm. The carriers are pre-molded in the conventional manner and are preferably spherical, but it is also possible to employ, for example, pre-molded carriers in the shape of rings or cylinders. The mean diameter of the pre-molded carrier is in most cases from 2 to 10 mm, preferably from 2 to 7 mm and especially from 3 to 6 mm. The materials have a rough surface, the recesses being mostly from 10 to 1,500 μm, especially from 20 to 750 μm.

Preferred active catalyst compositions for oxidizing acrolein to acrylic acid are those of the formula $Mo_{12}A_aB_bC_cD_dO_x$, where A is vanadium and/or tungsten, especially vanadium and tungsten, B is copper, iron, chromium and/or manganese, especially copper, or copper in combination with one or more of the other components B, C is antimony, niobium, tantalum and/or tin, D is lithium, sodium, potassium, rubidium, cesium and/or thallium and a is from 2 to 18, preferably from 0.5 to 12 for vanadium, from 0.2 to 6 for tungsten and from 2.5 to 18 for vanadium+tungsten, b is from 0.5 to 8, and for copper is preferably from 0.5 to 6, especially from 1 to 5, c is from 0 to 10 and d is from 0 to 0.5, preferably from 0 to less than 0.1, and x is from 41 to 127.75.

The component of group C as a rule does not improve the catalyst properties as far as the oxidation of acrolein to acrylic acid is concerned. This is also true of the component of group D, and higher concentrations of alkali metal oxides ($d>0.5$) in general reduce the activity, so that as a rule alkali metals are only present in the active catalyst composition in such concentration in such concentrations as result from using raw materials of commercial purity; for example, commercial grades of ammonium molybdate or molybdic acid of technical catalyst quality frequently contain up to 200, sometimes up to 500, ppm of potassium, whilst technical-grade carriers may contain up to 0.5% by weight of sodium and/or potassium.

The starting materials for the manufacture of the active catalyst composition are, in general, thermally easily decomposed salts of the components, of which an intimate mixture is prepared by, for example, mixing their aqueous solutions and then dehydrating the solution and drying the residue. Thereafter, the mixture is converted to the oxides by one or more calcinations at above the decomposition point of the salts and below or at the optimum final calcination temperature, this process being carried out in the absence of the molded carrier. Preferred easily decomposed salts are the ammonium salts of the oxy-acids of molybdenum, vanadium and tungsten, vanadyl oxalate, and the nitrates, oxalates, hydroxides, carbonates, sulfates, acetates and/or formates of the cationic components, of which aqueous solutions are preferably prepared at an elevated temperature, eg. at from 50° to 100° C., and preferably at a pH of from 2 to 6. On mixing, suspensions are in most cases obtained, which can be dried and can then, if necessary after addition of water, be homogenized, eg. by kneading, and densified. The calcination is carried out at from 140° to 600° C., preferably from 180° to 450° C. and especially from 230° to 420° C. In a preferred embodiment of the manufacture of the catalysts, the dehydrated mixtures of the easily decomposed salts are first calcined at from 180° to 350° C., especially at from 230° to 300° C., and then at from 350° to 600° C., preferably at from 370° to 450° C., and especially at from 380° to 420° C., in air. For the manufacture of certain active catalyst compositions, eg. those containing iron, it is sometimes of advantage to carry out the calcination in an inert atmosphere (eg. nitrogen) or a slightly reducing atmosphere (eg. a gas mixture containing propylene and/or acrolein).

After calcining the oxide mixture and comminuting it to a particle size of less than 150 μm, the active catalyst composition, preferably mixed with a wetting liquid which evaporates easily, is applied to the pre-molded carrier, the particle size of the pulverulent active catalyst composition being less than 150 μm, preferably less than 80 μm and especially less than 50 μm. The composition may be applied, for example, by granule coating or spraying the pre-molded, eg. spherical, carrier with a suspension of the active catalyst composition in water, the carrier being at from room temperature, ie. about 20° C., to 300° C. The thickness of the layer of active catalyst composition on the carrier surface should be from 10 to 1,500 μm, preferably from 20 to 750 μm and especially from 50 to 400 μm, corresponding to the finished catalyst containing from about 0.05 to 0.60 kg of active catalyst composition per liter (Bulk volume) of finished catalyst.

When applying the active catalyst composition to the premolded carrier it can be of advantage to add small amounts, in general from 0.5 to 20, preferably from 1 to 10, percent by weight of materials which improve the adhesion of the active composition to the carriers. Suitable materials of this nature are inorganic hydroxo salts and compounds which in aqueous solution hydrolyze to give hydroxides by hydroxo complexes and which are catalytically inert or are in any case a constituent of the active catalyst composition. Examples are aluminum chloride, molybdenum sulfide and/or basic aluminum salts, eg. basic aluminum nitrate. However, in the case of the active catalysts having the compositions stated above to be preferred, the addition of such materials is in general not necessary.

The carriers coated with the active composition are then dried, if necessary, at below 180° C., preferably below 150° C. In the case of granule coating, the pulverulent active catalyst composition is fed, at constant speed, onto the vigorously agitated, continuously moistened carrier in a rotary mixer or on a granulating disc.

The catalysts of the invention are outstandingly suitable for oxidizing acrolein and methacrolein with oxygen-containing gases, under otherwise conventional conditions, to give acrylic acid and methacrylic acid, respectively. The catalysts of the invention are distinguished by a particularly high selectivity and activity when used for the industrial manufacture of acrylic acid by oxidizing acrolein; surprisingly, the selectivity and activity achieved in tubes with diameters useful for production purposes, ie. 15 mm and above, are greater, under comparable conditions, than those achieved with catalysts disclosed in, for example, U.S. Pat. No. 3,956,377. Furthermore, the new catalysts show lower abrasion losses of catalytic composition, for example whilst being packed into a reactor, and have a particularly uniform composition and uniform thickness of the active layer. They are especially suitable for use with high space velocities of greater than 2,000 h$^{-1}$ and low water vapor concentrations of less than 20% by volume, and with linear gas velocities of greater than 100 cm/sec. especially in tubes having a diameter of from 15 to 40 mm at from 200° to 350° C. In the case of tubes having diameters greater than 20 mm it can be of advantage to dilute the catalyst with from 10 to 60% by volume of moldings of an inert material or of a catalyst of lower activity, so that in the direction of flow the activity increases from a value of from 40 to 80% of the maximum to 100% of the latter.

In the Examples which follow, parts are by weight, bearing the same relation to parts by volume as one kilogram to the liter. To test the catalytic properties of the catalysts from Examples 1 to 14, 40 ml of one of the catalysts are packed into a tube of 15 mm internal diameter and the tube is then heated to the test temperature in a salt bath. Per hour, 3.4 liters (S.T.P.) of acrolein, 28 liters (S.T.P.) of air, 30 liters (S.T.P.) of nitrogen and 25 liters (S.T.P.) of steam are passed through the tube. The analysis of the off-gas gives the conversions of acrolein and yields of acrylic acid, acetic acid and carbon oxides ($CO_x$) shown in the Tables.

EXAMPLES 1 to 9

(Active composition $Mo_{12}V_{4.6}W_{2.4}Cu_{2.2}O_{56.9}$; various carriers)

Manufacture of the catalysts:

65 parts of ammonium paratungstate, 54 parts of ammonium metavanadate and 212 parts of ammonium heptamolybdate are dissolved, in this sequence, in 2,500 parts of water at 95° C. A solution of 54 parts of copper nitrate in 125 parts of water is then added, the mixture is evaporated and the residue is dried at 110° C. It is then kneaded, with addition of 50 parts of water, for 3½ hours, dried for 4 hours at 250° C. in a rotary oven, and calcined for 3 hours at 395° C. The calcined composition is milled to a particle size less than 150 μm.

30 parts of the active pulverized catalyst composition mixed with from 10 to 30 parts of water are applied to 100 parts by volume (bulk volume) of magnesium silicate spheres of diameter 3 mm, and then dried at 100° C. (Example 1). To manufacture the catalysts of Examples 2 to 9, 100 parts by volume of the carriers stated for these Examples are used, and in other respects the procedure described above is followed. The catalysts are tested as described above; the results, together with the abrasion loss, are shown in Table 1. The abrasion loss is the proportion of active catalyst composition, in percent by weight of the composition present on the carrier, which is abraded under the following conditions: 50 parts by volume of catalyst are tumbled for 5 minutes at constant speed on a covered disc and the proportion abraded is then sieved off and weighed.

TABLE 1

| Example | Active composition particle size in μm | Carrier Nature | Carrier Open porosity, % | Carrier Proportion (in %) of macropores of 20–1,500 μm | Inner surface area m²/g | Catalyst: parts of active composition per part by volume of carrier | mean thickness of layer μm |
|---|---|---|---|---|---|---|---|
| 1 | <80 | Mg silicate spheres 3–3.5 mm | 0 | 0 | <<1 | 0.300 | 130 |
| 2 | <80 | SiO₂ spheres 3.5 mm | >50 | 8 | 622 | 0.300 | 175 |
| 3 | <50 | α-Al₂O₃ 3–5 mm | 3 | about 50 | 0.04 | 0.15 | 70 |
| 4 | <150 | α-Al₂O₃ spheres 3–3.5 mm | 34 | 84 | <1 | 0.300 | 125 |
| 5 | <80 | α-Al₂O₃ spheres 3–3.5 mm | 34 | 84 | <1 | 0.300 | 125 |
| 6 | <80 | α-Al₂O₃ spheres 3–3.5 mm | 34 | 84 | <1 | 0.224 | 105 |
| 7 | <50 | α-Al₂O₃ spheres 3–3.5 mm | 34 | 84 | <1 | 0.182 | 90 |
| 8 | <80 | mullite spheres 5–6 mm | 25 | 63 | 4.5 | 0.258 | 215 |
| 9 | <50 | mullite spheres 5–6 mm | 25 | 63 | 4.5 | 0.15 | 130 |

The surface recesses are <10 μm for the carrier of Example 1, <20 μm for the carrier of Example 2, from 50 to 250 μm for the carriers of Examples 3 to 7 and from 20 to 300 μm for the carriers of Examples 8 and 9.

Activity test

| Ex. | Bath temperature °C. | Conversion mole % | yield, mole % acrylic acid | yield, mole % acetic acid | $CO_x$ | Abrasion loss, % by weight |
|---|---|---|---|---|---|---|
| 1 | 289 | 99.5 | 93 | 2 | 4.5 | 7 |
| 2 | 275 | 94.5 | 84 | 1.7 | 8.5 | 5 |
| 3 | 282 | 99.1 | 93 | 1.6 | 4.5 | 2 |
| 4 | 279 | 97.4 | 92 | 1.4 | 4 | 3 |
| 5 | 275 | 98.4 | 93 | 0.9 | 4.5 | 2 |
|   | 277 | ~100 |   |   |   |   |
| 6 | 295 | 98.5 | 92 | 1.5 | 5 | 2 |
| 7 | 298 | 97.5 | 91.5 | 1.2 | 4.7 | 0.2–0.7 |
| 8 | 284 | 99 | 92.9 | 1.1 | 5 | 1.5 |
| 9 | 305 | 96.7 | 89.5 | 1.9 | 5.3 | 0.5 |

EXAMPLES 10 to 14

(Catalysts obtained from various active compositions)

Catalyst compositions of various constitutions (cf. Table 3) are manufactured by the method described for Examples 1 to 9, using the easily decomposed salts shown in Table 2. After calcining, the active composition is in each case milled to a particle size of less than 80 μm and sprayed, as an aqueous suspension with a weight ratio of active catalyst composition to water of from 1:1 to 1:2, onto the carrier spheres at from 25° to 80° C. The activity of the catalysts is tested as described above and the results are summarized in Table 3 below.

TABLE 2

| Easily decomposed salt | Parts by weight in Example | | | | |
|---|---|---|---|---|---|
|  | 10 | 11 | 12 | 13 | 14 |
| iron(III) nitrate | 44.5 | 222. | — | — | — |
| Mn-acetate-tetrahydrate | — | — | 30 | — | — |
| SnO₂ | — | — | — | 22.5 | — |

TABLE 2-continued

| Easily decomposed salt | Parts by weight in Example | | | | |
|---|---|---|---|---|---|
| | 10 | 11 | 12 | 13 | 14 |
| Ammonium dichromate | — | — | — | — | 7.5 |
| Copper(II) nitrate | 28.5 | 54 | 28.5 | 28.5 | 54 |
| Ammonium heptamolybdate | | | | 212 | |
| Ammonium metavanadate | 54 | 35 | 54 | 54 | 54 |
| Ammonium paratungstate | 65 | 32.3 | 65 | 65 | 65 |

TABLE 3

| Example | Active composition formula | Particle size $\mu m$ | Carrier | Parts of active composition per part by volume of carrier |
|---|---|---|---|---|
| 10 | $Mo_{12}V_{4.6}W_{2.4}Cu_{1.2}Fe_{1.1}O_{57.6}$ | <50 | $\alpha$-$Al_2O_3$, 3–4 mm, inner surface area <1 $m^2$/g, porosity = 34% proportion of pores of 20–1,500 $\mu m$ = 84%, surface recesses from 20 to 300 $\mu m$ | 0.3 |
| 11 | $Mo_{12}V_3W_{1.2}Cu_{2.2}O_{49.3}$ | <50 | $\alpha$-$Al_2O_3$, 3–4 mm, inner surface area <1 $m^2$/g, porosity = 34% proportion of pores of 20–1,500 $\mu m$ = 84%, surface recesses from 20 to 300 $\mu m$ | 0.3 |
| 12 | $Mo_{12}V_{4.6}W_{2.4}Cu_{1.2}Mn_{1.2}O_{57.1}$ | <20 | $\alpha$-$Al_2O_3$, 3–4 mm, inner surface area <1 $m^2$/g, porosity = 34% proportion of pores of 20–1,500 $\mu m$ = 84%, surface recesses from 20 to 300 $\mu m$ | 0.3 |
| 13 | $Mo_{12}V_{4.6}W_{2.4}Cu_{1.2}Sn_{1.2}O_{58.3}$ | <20 | $\alpha$-$Al_2O_3$, 3–4 mm, inner surface area <1 $m^2$/g, porosity = 34% proportion of pores of 20–1,500 $\mu m$ = 84% surface recesses from 20 to 300 $\mu m$ | 0.3 |
| 14 | $Mo_{12}V_{4.6}W_{1.2}Cu_{2.2}Cr_{0.6}O_{54.2}$ | <20 | $\alpha$-$Al_2O_3$, 3–4 mm, inner surface area <1 $m^2$/g, porosity = 34% proportion of pores of 20–1,500 $\mu m$ = 84%, surface recesses from 20 to 300 $\mu m$ | 0.3 |

| | | | Activity test | | | |
|---|---|---|---|---|---|---|
| Ex. | Thickness of layer, $\mu m$ | Bath temperature | Conversion, mole % | yield, mole % | | |
| | | | | acrylic acid | acetic acid | $CO_x$ |
| 10 | 125 | 298 | 97 | 90 | 1.5 | 5.5 |
| | | 302 | 100 | 91.5 | 2 | 7 |
| 11 | | 284 | 99.4 | 93 | 1.6 | 4.8 |
| 12 | | 290 | 99.3 | 92 | 1.1 | 6.2 |
| 13 | | 292 | 48.2 | 90.2 | 1.6 | 6.1 |
| 14 | | 288 | 98 | 91 | 1.4 | 5.6 |

EXAMPLE 15

1,000 ml of a spherical catalyst (sphere diameter about 5.3 mm), manufactured as described in Example 8, were packed into a steel tube of 4 m length and 25 mm diameter and the surrounding salt bath was heated at 286° C. (2nd stage). A catalyst specific for the conversion of propylene to acrolein was packed into an upstream reactor (first stage). This latter catalyst was precipitated by the method of Example 1 of German Laid-Open Application DOS No. 2,338,111, dried, calcined at 300° C., mixed with 2% by weight of graphite powder, molded to give 3×3 mm pellets and calcined for 1½ hours at 580° C. It has the composition $Mo_{12}BiIn_{0.1}Fe_2Ni_{6.5}P_{0.06}Si_{10}O_{6.03}$ and contained, relative to the above formula, 0.05 atom of potassium, as a natural impurity of the ammonium molybdate used as the raw material. The catalyst in the upstream reactor was diluted with 200 ml of 3 mm spheres of magnesium silicate in such a way that the proportion by volume of the catalyst increased linearly in the direction of flow from 60% to 100%. A mixture of 105 liters (S.T.P.) of fresh propylene, 1,000 liters (S.T.P.) of fresh air and 1,200 liters (S.T.P.) of purified off-gas from the second stage reactor was passed hourly over the catalyst of the upstream reactor. The gaseous mixture from the upstream reactor was then passed to the catalyst tube. According to analysis of the material leaving the catalyst tube (second stage), the yield of acrylic acid, based on fresh propylene employed, was 80.8 mole % and the yield of carbon oxides resulting from combustion of acrolein and propylene in the second stage was 3.5 mole %. Based on the acrolein (and acrylic acid) produced in the first stage, the yield of acrylic acid and carbon oxides was calculated to be, respectively, 93 and 3.9 mole %, the acrolein conversion being 98%.

EXAMPLE 16

The experiment of Example 15 is repeated, except that the second part of the reactor is packed with 832 ml of a catalyst manufactured as described in Example 5. The spherical catalyst (diameter about 3.5 mm) was diluted with 168 ml of 3 mm steatite spheres in such a way that the proportion by volume of the catalyst-coated spheres increased linearly in the direction of flow from 60% by volume to 100%. At a bath temperature of 283° C., yields of acrylic acid and CO of, respectively, 82.3 and 2.5 mole % based on fresh propylene employed, or of 95% and 2.9%, based on acrolein and acrylic acid formed in the first stage, were obtained. The acrolein conversion was 98 mole %.

COMPARATIVE EXPERIMENTS (A) 65 parts of ammonium paratungstate, 54 parts of ammonium metavanadate and 212 parts of ammonium heptamolybdate are dissolved, in the stated sequence, in 2,500 parts of water at 95° and a solution of 54 parts of copper nitrate in 125 parts of water is added to the solution, followed by 605 parts of α-aluminum oxide having a particle size of from 40 to 150 μm. The mixture is evaporated whilst being stirred, and is dried and calcined at from 230° to 250° C. Spheres of from 3 to 3.5 mm diameter are molded from the resulting calcined active composition, and are further calcined for 3 hours at 400° C. in air in a rotary oven. The activity of the catalyst (A) is tested as described immediately before Example 1. The results are shown in Table 4 below.

(B) 65 parts of ammonium paratungstate, 54 parts of ammonium metavanadate and 212 parts of ammonium heptamolybdate are dissolved, in the stated sequence, in 2,500 parts of water at 95° C., a solution of 54 parts of copper nitrate in 125 parts of water is added and 625 parts of α-aluminum oxide spheres of diameter from 3 to 3.5 mm, of the type described in Example 5, are impregnated with the mixture. They are then dried at 110° C. and calcined for 5 hours at 400° C. in a rotary oven. The catalyst (B) is tested as described immediately before Example 1; the results are shown in Table 4 below.

(C) 65 parts of ammonium paratungstate, 54 parts of ammonium metavanadate and 212 parts of ammonium heptamolybdate are dissolved, in the stated sequence, in 2,500 parts by weight of water at 95° C. and a solution of 54 parts of copper nitrate in 125 parts of water is added. 625 parts of α-aluminum oxide spheres of diameter from 3 to 3.5 mm, of the type described in Example 5, are sprayed with the mixture at 100°–110° C., whereupon the water evaporates. The impregnated spheres are then calcined for 4 hours at from 230° to 250° C. followed by 3 hours at 400° C. in a rotary oven. The catalyst obtained is tested as described immediately before Example 1; the results are shown in Table 4 below.

(D) Example 5 is repeated except that the particle size of the active composition is from 310 to 600 μm. The catalyst obtained is tested as described immediately before Example 1; the results obtained are shown in Table 4 below.

(E) Example 6 of German Laid-Open Application DOS No. 2,526,238 was repeated. To do this, 216 parts of $MoO_3$, 34.1 parts of $V_2O_5$, 27.59 parts of tungsten powder, 60.43 parts of Cu $(NO_3)_2.3$ $H_2O$ and 8.42 parts of SnO were suspended in 1,000 parts of water and the mixture was boiled under reflux for 20 hours. The suspension was then evaporated and the residue dried for 3 days at 115° C. A coherent dry mass was obtained, which was milled to give a powder. 45 parts of powder were applied to 100 parts of $Al_2O_3$ (SA 5.252 Alundum) of mean particle size ⅛ inch. The catalyst was tested as described immediately before Example 1. The results are shown in Table 4.

TABLE 4

| Comparative Example | Abrasion loss % by weight | Activity test | | | | |
|---|---|---|---|---|---|---|
| | | Bath temperature °C. | Conversion mole % | Yield, mole % | | |
| | | | | acrylic acid | acetic acid | $CO_x$ |
| A | 3 | 275 | 99 | 87 | 3 | 9 |
| B | (1) | 268 | 97 | 88 | 2.3 | 6.6 |
| C | 12–15 | 330 | 99 | 87 | 3 | 8 |
| D | >20(2) | 305 | 97 | 90.5 | 1.5 | 5 |
| E | 1–3 | 290 | 20.5 | 9 | 0.8 | 10.7 |
| | | 320 | 55.6 | 42 | 1.6 | 12 |

(1)A high proportion of the spheres was stuck together by the deposit of active composition, to form larger agglomerates and the catalyst was therefore industrially unusable in this form.
(2)(low adhesion of the active shell)

We claim:

1. A catalyst for the gas phase oxidation of acrolein or methacrolein with an oxygen-containing gas to give acrylic acid or methacrylic acid, respectively, said catalyst comprising a premolded inert carrier having a rough surface which has been coated with an active catalyst composition of the formula $Mo_{12}A_aB_bC_cD_dO_x$, wherein:

A is a mixture of V and W;

B is copper or copper in a mixture with a metallic element selected from the group consisting of Fe, Mn, Ni, and Cr;

C is a metallic element selected from the group consisting of Nb, Ta, Bi, Sb, Sn, Th, Ce, and U;

D is a metallic element selected from the group consisting of Li, Na, K, Rb, Cs and Tl; and a is from 0.5 to 12 for vanadium and from 0.2 to 6 for tungsten, the sum for vanadium and tungsten being from 2.5 to 18, b is from 0.5 to 8, the meaning of b for copper being 0.5 to 6, c is from 0 to 10, d is from 0 to less than 0.1 and x is from 41 to 127.75, said active catalyst composition being first manufactured, before its application to the carrier, from thermally easily decomposed salts of the metallic components by mixing aqueous solutions, slurries or moist solid masses of said easily decomposed salts, drying the mixture and calcining the dried composition at from 140° to 600° C., and said active catalyst composition in a particle size reduced to less than 150 micrometer then being applied together with water to the rough surface of the premolded carrier to form an active catalyst layer having a thickness of from 10 to 1,500 micrometer.

2. A catalyst as claimed in claim 1, wherein the carrier has a mean diameter of from 2 to 7 mm.

3. A catalyst as claimed in claim 1, wherein the carrier is in the shape of spheres.

4. A catalyst as claimed in claim 1, wherein the carrier has surface recesses of from 20 to 750 μm.

5. A catalyst as claimed in claim 1, wherein the inner surface area of the carrier is from 1 to 20 m²/g and its porosity is from 1 to 65%, and from 50 to 85% of the pores have a diameter of from 20 to 1,500 μm.

6. A catalyst as set forth in claim 1 wherein said carrier is selected from the group consisting of aluminum oxides, natural and synthetic silicates and aluminosilicates, silicon carbide, zirconium oxides and titanium oxides.

7. A catalyst as set forth in claim 1 wherein said active catalyst composition is applid to the carrier by spraying a suspension of the active catalyst composition in water onto the carrier.

8. A catalyst as set forth in claim 1 wherein said active catalyst composition is applied to the carrier by feeding said active catalyst composition having a particle size less than 150 micrometers at a constant speed onto vigorously agitated, continuously moistened carrier.

* * * * *